United States Patent [19]
Armstrong et al.
[11] 4,331,599
[45] May 25, 1982

[54] SPARINGLY WATER-SOLUBLE SALTS OF PENICILLANIC ACID 1,1-DIOXIDE

[75] Inventors: William W. Armstrong, Mill Neck, N.Y.; Charles E. Moppett, Mystic; Wendell W. Windisch, Groton, both of Conn.

[73] Assignee: Pfizer Inc., New York, N.Y.

[21] Appl. No.: 230,779

[22] Filed: Feb. 2, 1981

[51] Int. Cl.[3] .......... C07D 499/14
[52] U.S. Cl. .......... 260/245.2 R; 424/270; 424/271; 260/239.1
[58] Field of Search .......... 260/265.2 R; 424/270

[56] References Cited

U.S. PATENT DOCUMENTS

| | | | |
|---|---|---|---|
| 2,547,782 | 4/1951 | Rhodehamel et al. | 167/6 S |
| 2,585,432 | 2/1952 | Buckwalter | 260/239.1 |
| 2,627,491 | 2/1953 | Szabo et al. | 167/65 |
| 4,234,579 | 11/1980 | Barth | 424/246 |

FOREIGN PATENT DOCUMENTS 732559 6/1955 United Kingdom .

OTHER PUBLICATIONS

The Merck Index, p. 1005, (1976).

*Primary Examiner*—Nicholas S. Rizzo
*Attorney, Agent, or Firm*—Charles J. Knuth; Albert E. Frost; J. Trevor Lumb

[57] ABSTRACT

The 1:2 N,N'-dibenzylethylenediamine, the N-benzyl-2-phenylethylamine and the dibenzylamine salts of penicillanic acid 1,1-dioxide, a well-known betalactamase inhibitor, are sparingly soluble in water. Accordingly they are valuable as slow release (depot) forms of penicillanic acid 1,1-dioxide, particularly for use in conjunction with slow release (depot) forms of penicillin and cephalosporin antibiotics, in the chemotherapy of bacterial infections in mammals.

2 Claims, No Drawings

SPARINGLY WATER-SOLUBLE SALTS OF PENICILLANIC ACID 1,1-DIOXIDE

BACKGROUND OF THE INVENTION

This invention relates to the chemotherapy of bacterial infections in mammalian subjects. More particularly, it relates to sparingly water-soluble salts of the beta-lactamase inhibitor penicillanic acid 1,1-dioxide, and their use in conjunction with beta-lactam antibiotics in the chemotherapy of bacterial infections in mammals.

One of the most well-known and widely used of the classes of antibacterial agents is the class known as the beta-lactam antibiotics. These compounds are characterized in that they have a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which cleave the beta-lactam ring of penicillins and cephalosporins to give products which are devoid of antibacterial activity. However, certain substances have the ability to inhibit beta-lactamases, and when a beta-lactamase inhibitor is used in combination with a penicillin or cephalosporin it can increase or enhance the antibacterial effectiveness of the penicillin or cephalosporin against certain microorganisms. One useful beta-lactamase inhibitor is penicillanic acid 1,1-dioxide, the compound of the formula I:

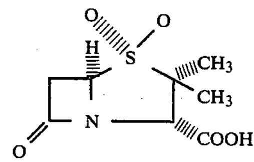

(I)

U.S. Pat. No. 4,234,579 describes the preparation of penicillanic acid 1,1-dioxide, and methods for its use as a beta-lactamase inhibitor in combination with beta-lactam antibiotics. Additionally, U.S. Pat. No. 4,234,579 discloses salts of penicillanic acid 1,1-dioxide, including amine salts. However, the amine salts disclosed in U.S. Pat. No. 4,234,579 are relatively soluble in water, and they are rapidly excreted from the mammalian subject after parenteral administration. It has now been found that certain amine salts of penicillanic acid 1,1-dioxide are sparingly soluble in water, and after parenteral administration to a mammalian subject they give prolonged blood levels of penicillanic acid 1,1-dioxide. These sparingly soluble salts of penicillanic acid 1,1-dioxide are the 1:2 N,N'-dibenzylethylenediamine salt, the N-benzyl-2-phenylamine salt and the dibenzylamine salt.

The 1:2 N,N'-dibenzylethylenediamine, the N-benzyl-2-phenylethylamine and the dibenzylamine salts of several penicillin antibiotics e.g. benzylpenicillin, have been prepared. See further: U.S. Pat. Nos. 2,627,491 and 2,585,432 and British Pat. No. 732,559.

SUMMARY OF THE INVENTION

This invention provides the following salts:

(a) the 1:2 N,N'-dibenzylethylenediamine salt of penicillanic acid 1,1-dioxide;

(b) the N-benzyl-2-phenylethylamine salt of penicillanic acid 1,1-dioxide; and (c) the dibenzylamine salt of penicillanic acid 1,1-dioxide.

The above salts are sparingly soluble in water, and therefore they are of value as slow-release forms of the well-known beta-lactamase inhibitor, penicillanic acid 1,1-dioxide, in the chemotherapy of bacterial infections in mammals.

The preferred salt of this invention is the 1:2 N,N'-dibenzylethylenediamine salt of penicillanic acid 1,1-dioxide.

DETAILED DESCRIPTION OF THE INVENTION

The compounds of this invention are salts of penicillanic acid 1,1-dioxide, which is the compound of the formula

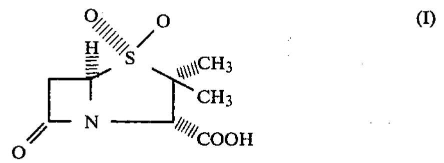

(I)

The 1:2 N,N'-dibenzylethylenediamine salt of penicillanic acid 1,1-dioxide is the salt formed from N,N'-dibenzylethylenediamine and two molar equivalents of penicillanic acid 1,1-dioxide; the N-benzyl-2-phenylethylamine salt of penicillanic acid 1,1-dioxide is the salt formed from N-benzyl-2-phenylethylamine and one molar equivalent of penicillanic acid, 1,1-dioxide; and the dibenzylamine salt of penicillanic acid 1,1-dioxide is the salt formed from dibenzylamine and one molar equivalent of penicillanic acid 1,1-dioxide. N,N'-dibenzylethylenediamine is also known as benzathine and as DBED; N-benzyl-2-phenylethylamine is also known as benethamine.

The salts of this invention can be prepared by conventional methods, well-known to one skilled in the art. For example, the penicillanic acid 1,1-dioxide and the amine can be contacted in substantially stoichiometric proportions, in an appropriate inert solvent, or a mixture of inert solvents, at a temperature in the range from −20° to 30° C. Salt formation takes place quite rapidly and is complete within a few minutes. Appropriate inert solvents are those which substantially dissolve the penicillanic acid 1,1-dioxide and the amine, and which do not adversely interact with either the penicillanic acid 1,1-dioxide, the amine or the salt. Typical solvents are lower alkanols, such as methanol and ethanol; low molecular weight ketones, such as acetone and methyl isobutyl ketone; low molecular weight ethers, such as diethyl ether and diisopropyl ether; low molecular weight esters, such as ethyl acetate and butyl acetate; acetonitrile; formamide, N,N-dimethylformamide, N,N-dimethylacetamide, dimethyl sulfoxide; and mixtures thereof. The salt product is recovered simply by filtration, by evaporation of the solvent, or by precipitation followed by filtration, as appropriate, and it can be purified further, if desired, by classical techniques such as recrystallization. Although solvents in which the salt is either freely soluble or sparingly soluble can be used, solvents in which the salt is sparingly soluble are generally preferred.

A variation on the aforesaid method for preparing the salts of this invention involves contacting substantially stoichiometric quantities of a water-soluble salt of penicillanic acid 1,1-dioxide with a water-soluble salt of the amine, in a substantially aqueous solvent system, at a temperature in the range from −20° to 30° C., and at a concentration at which substantially all the salt product precipitates. The product salt can then be recovered by filtration. Salts of the penicillanic acid which can be used for this purpose are alkali metal salts, such as sodium and potassium salts; and low molecular weight amines, such as triethylamine and tributylamine salts. Salts of the amine reactant which can be used are the hydrohalides, such as the hydrochloride and the hydrobromide; and salts with simple aliphatic carboxylic acids, such as acetic acid and propionic acid.

A further variation for preparing the salts of this invention which is possible involves contacting substantially stoichiometric quantities of penicillanic acid 1,1-dioxide with a salt of the amine reactant formed from a weak acid, at a temperature in the range from −20° to 30° C., in a solvent which dissolves the penicillanic acid 1,1-dioxide and the amine salt reactant but in which the salt of the invention is sparingly soluble. Typical salts of the amine reactant which can be used for this purpose are simple aliphatic carboxylic acids, such as acetic acid, propionic acid, butyric acid, isobutyric acid, isocaproic acid, caproic acid and 2-ethylhexanoic acid. Typical solvents which can be used are lower alkanols, such as methanol and ethanol; low molecular weight ketones, such as acetone and methyl ethyl ketone; low molecular weight ethers, such as diethyl ether and diisopropyl ether; low molecular weight esters, such as ethyl acetate and butyl acetate; acetonitrile; and mixtures thereof.

As indicated hereinbefore, the salts of this invention act as slow-release forms of penicillanic acid 1,1-dioxide. Thus administration of a salt of this invention to a mammalian subject gives sustained blood levels of penicillanic acid 1,1-dioxide. Consequently, the salts of this invention are especially useful for co-administration to a mammalian subject with slow-release forms of beta-lactam antibiotics, such as penicillin and cephalosporin compounds which are sparingly soluble in water. Thus, the salts of this invention can conveniently be administered to a mammalian subject as a single dose at approximately the same time as the subject first receives a dose of a sparingly water-soluble penicillin or cephalosporin antibiotic. Subsequent doses can be given as necessary to maintain the desired blood levels of penicillanic acid 1,1-dioxide, while continuing to give the penicillin or cephalosporin compound at appropriate intervals. Alternatively, a salt of this invention can be co-formulated with the penicillin or cephalosporin compound with which it is the co-administered, and the two agents are thereby given simultaneously. The dose is repeated as necessary to sustain the desired blood levels for the required length of time. The weight ratio of the active ingredients will normally be 1:6 to 6:1, and preferably 1:3 to 3:1.

When considering use of a salt of this invention as a slow-release form of penicillanic acid 1,1-dioxide, it is preferably administered intramuscularly or subcutaneously. For this purpose, it is usual to prepare an aqueous or non-aqueous suspension of a salt of this invention in substantially the same manner as that currently used for formulation of a sparingly water-soluble beta-lactam antibiotic such as ampicillin trihydrate or benzathine penicillin G. The proportional ratio of a salt of this invention and the carrier can vary, depending on the dosage contemplated. However, suspensions of a salt of this invention will usually contain from 50 to 200 milligrams of activity of a salt of this invention per milliliter of suspension. In the case of aqueous suspensions, small amounts of other ingredients conventionally used in preparing aqueous suspensions can also be added. For example, it is possible to add emulsifiers, such as lecithin, sorbitan mono-oleate, sorbitan monopalmitate and polyoxyethylene (20) sorbitan mono-oleate; hydrocolloids, such as carboxymethyl cellulose; dispersing agents, such as polyvinylpyrrolidone; and preservatives, such as sodium benzoate, methylparaben and propylparaben. Additionally it is preferable to buffer the suspension to a pH in the range from 6 to 7, and a sodium citrate/citric acid buffer is convenient for this purpose. Non-aqueous suspensions are commonly made using propylene glycol diester (dicaprylate/caprate) containing a small amount of phenol.

A salt of this invention can be used in conjunction with a sparingly water-soluble penicillin or cephalosporin compound in a human subject, and also in domestic pets (e.g. cats and dogs) and large farm animals (e.g. horses, sheep, cattle and pigs). The prescribing physician or veterinarian will ultimately decide the appropriate dosage, and this will vary according to a variety of factors, such as the weight and response of the individual subject, as well as the nature and severity of the subject's symptoms. However, intramuscular or subcutaneous doses of from about 4 to about 40 mg. per kilogram of body weight will normally be used. The dose will be repeated when the blood level of penicillanic acid 1,1-dioxide has fallen below the desired level. Also, dosing will continue until the desired therapeutic effect has been obtained.

Typical sparingly water-soluble penicillin antibiotics with which a salt of this invention can be co-administered are the 1:2 N,N'-dibenzylethylenediamine salts of penicillin G and penicillin V and ampicillin trihydrate.

The following examples are being provided to further illustrate this invention; however they should not be construed as limiting the scope of the invention in any way. Infrared spectra were measured as potassium bromide discs, and major absorptions are reported in wave numbers ($cm^{-1}$). Proton magnetic resonance spectra were measured as solutions in perdeutero dimethyl sulfoxide, at 100 MHz, and absorptions are reported in parts per million downfield from internal trimethylsilane. The following abbreviations for peak shapes are used: s, singlet; m, multiplet. Proton decoupled $^{13}C$ magnetic resonance spectra were measured as solutions in perdeutero dimethyl sulfoxide, and absorptions are reported in parts per million downfield from internal tetramethylsilane.

EXAMPLE 1

1:2 N,N'-Dibenzylethylenediamine Salt of Penicillanic Acid 1,1-Dioxide

A solution of 201.7 g. of sodium penicillanate 1,1-dioxide in 1,000 ml. of distilled water, water was cooled to ca. 8° C., and then a cooled (ca. 10° C.) solution of 156.2 g. of N,N'-dibenzylethylenediamine diacetate in 1,400 ml. of distilled water was added dropwise, with vigorous stirring during 12 to 15 minutes. Stirring was continued for a further 20 minutes at 5°–8° C. after the addition ceased, and then the precipitate was recovered by filtration. The solid which was recovered was washed well with cold water and then it was dried at 40° C. under vacuum. This afforded 255.6 g. of the title salt, m.p. 165°–66° C. (dec.). By Karl Fischer titration, this material contained 5.03% of water. The infrared spectrum showed absorptions at 3546, 3333, 2666, 2409, 1769, 1626, 1562, 1398, 1111 and 754 $cm^{-1}$. The proton magnetic resonance spectrum showed absorptions at 1.31 (s, 6H), 1.38 (s. 6H), 3.04 (s, 4H), 3.08 (m, 2H), 3.26 (m, 2H), 3.90 (s, 2H), 4.04 (s, 4H), 4.93 (m, 2H) and 7.42 (m, 10H) ppm. The proton decoupled $^{13}C$ magnetic resonance spectrum showed absorptions at 18.4831, 19.9920, 36.9787, 43.6649, 50.6570, 60.6107, 62.6252, 64.7556, 128.599, 129.627, 133.507, 169.961 and 172.023 ppm.

EXAMPLE 2

N-Benzyl-2-phenylethylamine Salt of Penicillanic Acid 1,1-Dioxide

A solution of 885 mg. of penicillanic acid 1,1-dioxide in 125 ml. of diethyl ether was added, with stirring, during about 20 minutes, to a solution of 828 mg. of N-benzyl-2-phenylethylamine in 100 ml. of diethyl ether. The mixture was stirred an additional 20 minutes and the solid was recovered by filtration. The solid was washed with ether and then it was dried under vacuum. This afforded 1.57 g. of the title compound m.p. 161°–3° C. (dec.). By Karl Fischer titration this material contained 1.33% of water. The infrared spectrum showed absorptions at 3067, 2816, 2380, 1785, 1600, 1298, 1111, 784, 751 and 699 $cm^{-1}$. The proton magnetic resonance spectrum showed absorptions at 1.38 (s, 3H), 1.52 (s, 3H), 3.04 (s, 4H), 3.12 (m, 1H), 3.54 (m, 1H), 3.90 (s, 1H), 4.10 (s, 2H), 4.94 (m, 1H) and 7.28 (m, 10H) ppm. The proton decoupled $^{13}C$ magnetic resonance spectrum showed absorptions at 18.5835, 20.0678, 31.9754, 36.8485, 47.7418, 50.0436, 60.5537, 62.6515, 65.1919, 126.547, 128.506, 129.710, 133.008, 137.697, 169.570 and 171.986 ppm.

EXAMPLE 3

Dibenzylamine Salt of Penicillanic Acid 1,1-Dioxide

A solution of 1.275 g. of sodium penicillanate 1,1-dioxide in ca. 3 ml. of water was added to a solution of dibenzylamine hydrochloride in 37 ml. of water, with stirring. Stirring was continued for a further 20 minutes, and the solid was recovered by filtration. The solid was washed with water, and then it was dried at room temperature under vacuum. This afforded 1.102 g. of the title compound, m.p. 159°–60° C. By Karl Fischer titration, the product contained 2.95% of water. The infrared spectrum showed absorptions at 4347, 3333, 2985, 2777, 2597, 2439, 1769, 1587, 1398, 1111, 775 and 669 $cm^{-1}$. The proton magnetic resonance spectrum showed absorptions at 1.34 (s, 3H), 1.38 (s, 3H), 3.30 (m, 2H), 3.90 (s, 1H), 4.06 (s, 4H), 4.94 (m, 1H) and 7.40 (m, 10H) ppm. The proton decoupled $^{13}C$ magnetic resonance spectrum showed absorptions at 18.5613, 20.0192, 36.9093, 50.0135, 60.5833, 62.6788. 65.0384, 128.457, 129.703, 133.388, 169.426 and 171.936 ppm.

EXAMPLE 4

Dibenzylamine Salt of Penicillanic Acid 1,1-Dioxide

A mixture of 38.4 ml. of dibenzylamine, 500 ml. of distilled water and 15 ml. of acetic acid was stirred for 2 hours at room temperature, and the solution so obtained was added dropwise, with rapid stirring, during ca. 20 minutes, to a solution of 62 g. of sodium penicillanate 1,1-dioxide in 300 ml. of distilled water. Stirring was continued for a further 10 minutes, and then the precipitate was collected by filtration. The solid was dried at room temperature overnight, to give 68 g. of the title compound, m.p. 149°–51° C. (dec.). By Karl Fischer titration, this material contained 6.11% water.

EXAMPLE 5

Aqueous Formulation

A typical formulation contains the following ingredients:

| Ingredient | Weight (in grams) |
|---|---|
| Sodium benzoate | 0.3 |
| Sodium citrate | 0.45 |
| Citric acid | 0.05 |
| Lecithin | 0.3 |
| Sodium carboxymethyl cellulose | 0.5 |
| Polyoxyethylene (20) sorbitan mono-oleate | 0.07 |
| 1:2 N,N'-Dibenzylethylenediamine salt of penicillanic acid 1,1-dioxide | 15.0 |

The above ingredients are combined and the volume is made up to 100 ml. with deionized water. An appropriate volume is used to provide the dosage required.

EXAMPLE 6

Non-aqueous Formulation

| Ingredient | Amount |
|---|---|
| 1:2-N,N'-Dibenzylethylenediamine salt of penicillanic acid 1,1-dioxide | 9.06 g. |
| Ampicillin trihydrate | 13.8 g. |
| Phenol | 0.5 g. |
| Propyleneglycol diester (dicaprylate/caprate) | 80 ml. |

The above ingredients are thoroughly mixed. An appropriate volume is used to provide the dosage required.

We claim:

1. A compound selected from the group consisting of:
(a) the 1:2 N,N'-dibenzylethylenediamine salt of penicillanic acid 1,1-dioxide;
(b) the N-benzyl-2-phenylethylamine salt of penicillanic acid 1,1-dioxide; and
(c) the dibenzylamine salt of penicillanic acid 1,1-dioxide.

2. The 1:2 N,N'-dibenzylethylenediamine salt of penicillanic acid 1,1-dioxide, a compound according to claim 1.

* * * * *